United States Patent [19]
Gollestani

[11] Patent Number: 4,802,469
[45] Date of Patent: Feb. 7, 1989

[54] THERAPEUTIC BODY SUIT

[76] Inventor: Maria Gollestani, P.O. Box 2388, Kailua-Kona, Hi. 96745

[21] Appl. No.: 80,985

[22] Filed: Aug. 3, 1987

[51] Int. Cl.$^4$ .............................................. A61F 5/24
[52] U.S. Cl. .................................. 128/98.1; 128/96.1; 2/118; 2/408; 2/DIG. 6
[58] Field of Search .................... 128/96.1, 99.1, 98.1, 128/100.1, 101.1, 159, 133, 134, DIG. 15; 450/62, 82, 83, 84, 85, 86, 88; 2/DIG. 6, 408, 118, 70, 95, 71, 102, 72, 103, 67, 2

[56] References Cited

U.S. PATENT DOCUMENTS

| | | | |
|---|---|---|---|
| 1,488,339 | 3/1924 | Grosberg | 128/159 |
| 1,650,062 | 11/1927 | Butterly | 128/159 |
| 2,343,607 | 3/1944 | Wrigley | 450/86 X |
| 2,612,642 | 10/1952 | Robins | 2/67 X |
| 2,882,907 | 4/1959 | Puliafico | 450/88 X |
| 3,154,082 | 10/1964 | Cape | 2/DIG. 6 X |
| 3,189,028 | 6/1965 | Dormire | 128/DIG. 15 X |
| 3,207,155 | 9/1965 | Casey | 128/159 |
| 3,503,405 | 3/1970 | Porco | 2/408 X |
| 3,561,442 | 2/1971 | Goswitz | 128/DIG. 15 X |
| 3,628,539 | 12/1971 | Fredricks | 450/86 X |
| 3,691,564 | 9/1972 | LaMarre et al. | 2/2 |
| 3,712,308 | 1/1973 | Herbener | 2/408 X |
| 4,022,197 | 5/1977 | Castiglia | 128/96.1 X |
| 4,398,538 | 8/1983 | Johnson | 2/67 X |
| 4,412,357 | 11/1983 | Mincher | 2/118 |
| 4,675,918 | 6/1987 | O'Brien | 2/DIG. 6 X |
| 4,703,750 | 11/1987 | Sebastian et al. | 2/DIG. 6 X |

Primary Examiner—Robert A. Hafer
Assistant Examiner—Kevin G. Rooney

[57] ABSTRACT

The invention is a therapeutic body suit designed to produce therapeutic pressure on the abdominal and lower abdominal body areas as an aid to healing after certain types of surgery including: liposuction abdominal plasty; hysterectomy; cesarean section; mastectomy and breast surgery; and hernia. This invention may be utilized on women and men. The invention consists of three major components. The first component is a body suit designed to provide theraputic pressure. The second component is an elastic binding surrounding the body suit with detachable and adjustable ends designed to enhance the therapeutic pressure of the body suit. The third component is a breathing elastic crotch therapeutically supporting binding attached in a removable manner to the second component.

7 Claims, 1 Drawing Sheet

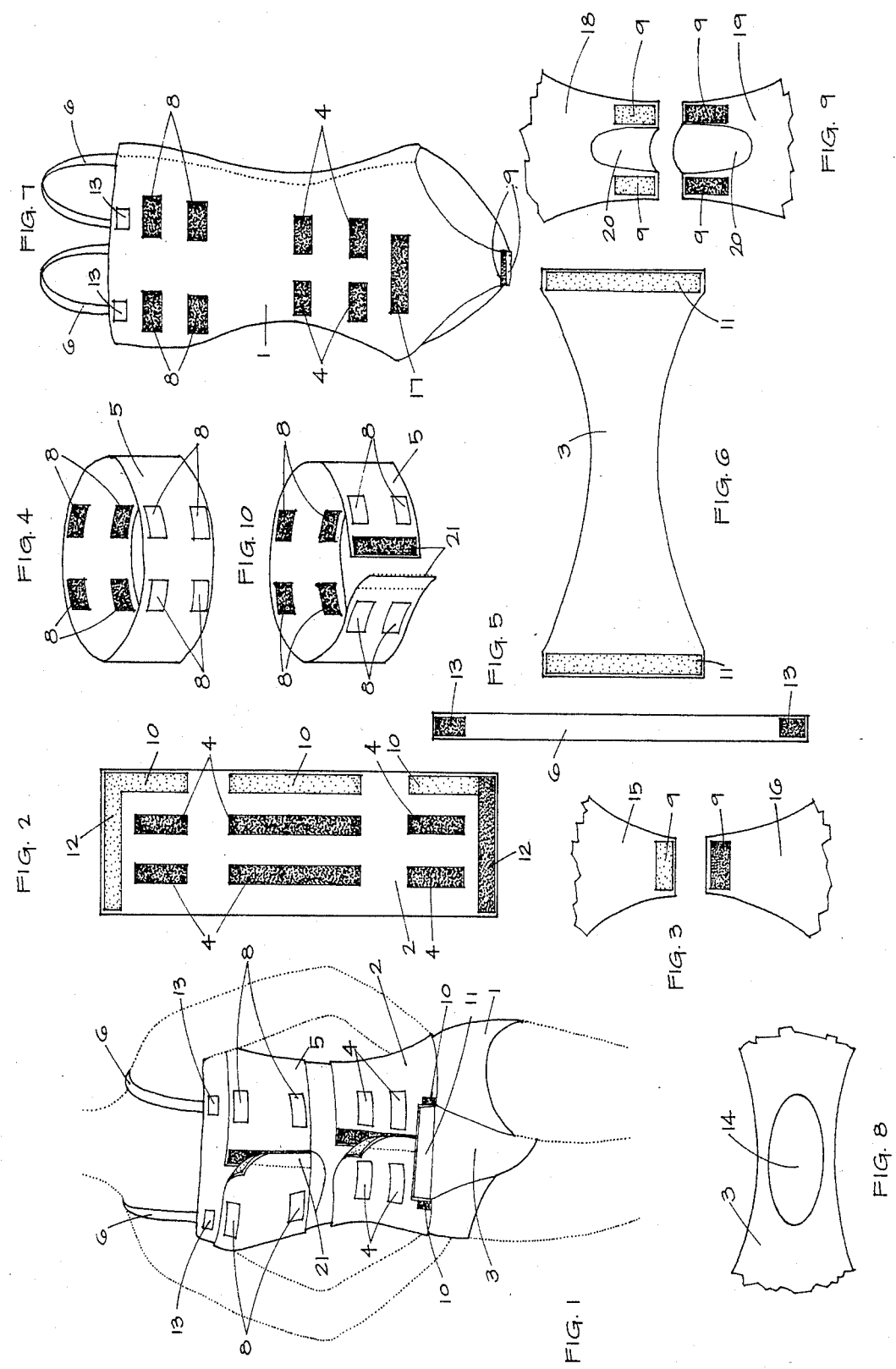

THERAPEUTIC BODY SUIT

FIELD OF ART

This device pertains to field of medical equipment; to subclass of artificial abdominal supporting prosthesis designed to temporarily exert pressure as an aid to medical and post-surgical healing.

BACKGROUND OF THE INVENTION

Certain types of surgery including liposuction; abdominal plasty; hysterectomy; mastectomy; cesarean section & breast surgery; and hernia repairs result in the separation of certain soft body tissue and swelling. Post-surgical healing for this tissue is promoted with the use of devices designed to exert certain therapeutic pressure externally about the affected body area. Present day devices consist of elastic bands of one of the three following types: (1) all elastic bands attached in an adjustable manner about the circumference of the abdomen capable of stretching about the length and width of the band; (2) all adjustable elastic bands attached as in 1, but containing attached restrictions permitting stretching about the length only, not the width; (3) bands as cited in 1 and 2 further including separate elastic crotch supporting bands.

Limitations of the prior art cited above include (1) inability of the devices to consistently remain in position with body movements occurring during daily living; (2) inability of the devices to comfortably transition from areas of the desired therapeutic pressure, to surrounding areas of non-pressure.

BRIEF DESCRIPTION OF THE DRAWINGS

FIG. 1 is a frontal view of the body suit with the waist binding, crotch binding, and brassiere in wearing position.

FIG. 2 shows the waist binding as viewed flat from it's interior side.

FIG. 3 shows the body suit interconnecting crotch ends from their exterior side.

FIG. 4 is a frontal perspective view of the brassiere with attachments bases located upon the interior surface.

FIG. 5 is a top view of the shoulder straps.

FIG. 6 shows the crotch binding as viewed flat from it's exterior surface.

FIG. 7 is a frontal view of the body suit showing the location of attachment bases for various bindings and other components.

FIG. 8 shows the center portion of the men's crotch binding with an integrated pouch for male genitalia.

FIG. 9 shows the male version of the body suit interconnecting crotch ends with a male genitalia pouch section between two attachment bases on each crotch end.

FIG. 10 is a frontal view of the brassiere version with adjustable center front closure capability utilizing attachment bases mounted to each frontal end.

BRIEF DESCRIPTION OF INVENTION COMPONENTS

1. Body Suit
2. Waist Binding
3. Crotch Binding
4. Waist Binding attachment bases for body suit
5. Brassiere
6. Shoulder Strap
8. Body suit attachment bases for brassiere
9. Body suit attachment bases for crotch interconnection
10. Waist binding bases for crotch binding
11. Crotch binding bases for body suit or waist binding
12. Waist binding adjustable interconnecting bases
13. Shoulder strap attachment bases for body suit
14. Male pouch for crotch binding.
15. Crotch interconnection front
16. Crotch interconnection rear
17. Body suit attachment base for crotch binding
18. Crotch interconnection front—male version
19. crotch interconnection rear—male version
20. male pouch section
21. brassiere adjustable closure interconnecting bases

DETAILED DESCRIPTION OF THE INVENTION

Body Suit

The Body Suit 1 of FIGS. 1 and 7 is constructed by sewing, heat or electric bonding, or other suitable constructions means utilizing a breathable elastic material designed to provide some therapeutic pressure about all contacted surfaces. The purpose of body suit 1 is to provide therapeutic pressure to those body surfaces it comes in contact with, as well as to provide a supporting structure for (1) elastic waist binding 2 of FIGS. 1 and 2; (2) crotch supporting binding 3 of FIGS. 1, 3 and 8; and (3) brassiere 5 of FIGS. 1 and 4. Body suit 1 is worn with or without supporting shoulder straps 6 of FIGS. 1, 5 and 7.

Body suit 1 is constructed from a thin elastic breathable material which may be either single or multi-layered. This disclosure does not specify any specific constructions materials, however suitable materials may include material types utilized for supporting girdles of the "Lyra Spandex" type or other suitable girdle fabric.

Body suit 1 has firmly attached to it one or more attaching bases 4 of FIG. 7 located upon the central outer front and back surfaces. The purpose of bases 4 of FIG. 7 are to provide rigid and removable attachment of elastic waist binding 2 of FIGS. 1, and 2 to prevent undesired repositioning of the waist binding.

Body suit 1 further has firmly attached optional attaching bases 17 located in the front and rear of body suit 1 as shown in FIG. 7. The purposes of attaching bases 17 of FIG. 7 are to provide rigid and removable attachment of the crotch supporting binding 3 of FIGS. 1, 3 and 8.

The body suit 1 further has rigidly attached to the inner upper surfaces attached bases 13 of FIGS. 1 and 7 for attachment of a removable brassiere 5 of FIGS. 1 and 4. Brassiere 5 is constructed of additional materials similar to those utilized in the body suit, but specifically containing close-fitting cups designed to support the female breasts. FIG. 10 shows an alternative version of brassiere 5 with adjustable center front closure capability utilizing adjustable closure interconnecting bases attached to each center front end. The additional upper body support provided with the use of brassiere 5 permits the body suit to be worn without the detachable straps 6 of FIGS. 1, 2, and 3. However, these straps are helpful in providing support to the upper body and female breasts when the brassiere 5 is not utilized concurrently. FIGS. 1, 4, and 7 show the attachment of brassiere to the exterior of body suit 1. This disclosure also provides for and alternative arrangement of attaching either the closed brassiere 5 of FIG. 4, or center front opening brassiere 5 of FIG. 10 to the body suit 1. In this alternative, brassiere 5 is attached to the interior of body suit 1 by (1) mounting body suit attachment bases 8 of FIG. 7 to the interior surface of body suit 1, and (2) by mounting brassiere attachment bases 8 of FIG. 4 to the exterior surface of brassiere 5 of FIG. 4.

The female version of the body crotch portion of body suit 1 is constructed in a manner wherein the portion of the front crotch piece and rear crotch piece are separate, but have attachment bases firmly attached to them wherein the front crotch piece 15 of FIG. 3 and rear crotch piece 16 of FIG. 3 are capable of attaching to each other in an adjustable manner, permitting a variation of pressure to be adjusted with the attachment and fastening of the two crotch pieces as shown in 9 of FIGS. 2 and 3.

The body crotch portion of the male version of body suit 1 is constructed in a manner wherein the front crotch piece 18 of FIG. 9 consists of two attachment bases 9 with a section of the male genitalia support pouch 20 located between them, and the rear crotch piece 19 of FIG. 9 consists of two attachment bases 9 with the second section of the male genitalia supporting pouch 20 located between. The attachment of the front body crotch section 18 to the rear male crotch piece section 19 results with the overlapping of the two male genitalia supporting pouch sections 20 creating the effect of a full male genitalia supporting pouch. The advantage of this arrangement is to provide for adjustable therapeutic pressure to the male crotch area while permitting comfortable and adjustable support of the male genitalia.

The body suit 1 may be utilized as a swim suit to maintain therapeutic body surface pressure while immersed in water, and may further be decorated with appropriate design work to enhance attractiveness.

Elastic Binding

The second component is the elastic waist binding 2 of FIGS. 1 & 2. The purpose of elastic waist binding 2 is to provide additional abdominal pressure above and beyond that provided by the body suit 1 of FIGS. 1, and 7.

Elastic waist binding 2 is constructed as a one piece elastic band with fastener bases 12 of FIGS. 1 and 2 rigidly attached to both ends in a manner permitting the binding ends to be adjusted and joined, or separated in a manner permitting the binding to exert elastic pressure on those areas in contact with it.

Elastic waist binding 2 is designed to be attached after body suit 1 of FIGS. 1 and 7 is donned. The elastic waist binding 2 of FIGS. 1 and 2 fastener bases 4 of FIG. 1 and 2 firmly attached to different inner surface locations designed to align, contact, and attach to matching fastener bases firmly attached to the front and rear of body suit 1.

During use of the elastic waist binding 2, the therapeutic pressure exerted upon the body by body suit 1 produces a smooth and consistently smooth surface characteristic to provide a firm foundation for the mounting of elastic waist binding 2. After mounting of waist binding 2, the edges of elastic waist binding 2 are restricted from contacting, rubbing, and irritating body skin and causing extra unnecessary swelling by the surface of body suit 1 during body motion or daily activity. Attachment of elastic waist binding 2 to the outside of body suit 1 with the fasteners further prevents the movement or dislocation of the elastic waist binding away from the desired body location.

Crotch Binding

The third component is the crotch binding 3 shown FIGS. 1, 6 and 8. The purpose of crotch binding 3 is to therapeutically support the lower abdominal or anatomical crotch area during post-surgical recovery.

Crotch binding 3 of FIGS. 1, 6 and 8 consists of an elastic binding constructed of breathing elastic materials which are wide at the ends and narrow in the center. The male version of crotch binding 3 is, in addition to the advantages described above, constructed with pouch 14 of FIG. 8 to provide support for the male genitalia.

Crotch binding 3 of FIGS. 1, 6 and 8 contain attachment bases at both ends to firmly attach to matching attachment bases located either (1) on the body suit as shown in number 17 of FIG. 7, or (2) on the elastic waist binding 2 with number 10 of FIGS. 1 and 2. Thus crotch binding 3 of FIGS. 1, 6 and 8 may be worn independently of elastic waist band 2 of FIGS. 1 and 2.

Conclusion

It is the intent of this disclosure to include all alternatives and variations which are obvious to the concepts described herein.

I claim:

1. A body suit providing therapeutic pressure for post-surgical or other medical uses comprising:
    (a) at least one section of flat breathing elastic material joined together to surround the abdominal areas below the shoulders, and to further cover the body from the breasts and upper back to the lower crotch, with openings for the legs to depend through;
    (b) shoulder straps for shoulder and breast support;
    (c) two separable crotch bottom ends with each end having attached to it an attachment base where the base of the first end may be attached or separated from the base of the second end;
    (d) the upper front and rear of the body suit having firmly attached to one of the interior and the exterior; attachment bases for removable attachment of a breast supporting brassiere;
    (e) the central front and back of the body having firmly mounted at least one attachment base to provide removable attachment of an elastic waist binding;
    (f) the front and rear lower waist areas of the body suit having firmly attached at least one attachment base to provide removable attachment of a crotch supporting binding; wherein said attachment bases permit tandem use of the crotch binding independently of an elastic waist binding;
    (g) an elastic waist binding constructed of flat breathing elastic material with attachment bases fixed to the rear interior back area which contact and attach to the attachment bases located on the central back of the body suit; the elastic waist binding further having one attachment base fixed to each of its two ends which connect to each other in an adjustable manner to provide additional pressure above and beyond that provided by the body suit, but in tandem with the body suit to the abdominal area it surrounds; the elastic waist binding further having attachment bases fixed to it and located at the lower central front and rear areas for attachment of a crotch binding;

(h) a crotch binding constructed of flat breathing elastic materials which is wider at its ends and tapers towards its center; the crotch binding ends having attachment bases mounted thereon for removable attachment to the elastic waist binding.

2. The device as claimed in claim 1 further having two attachment bases which are attached to the top portion of the front body suit, and two attachment bases attached to the top rear of the body suit; and two removable shoulder straps with attachment bases attached to each end of each shoulder strap wherein the shoulder straps may be removed from the body suit with the brassiere providing upper body support for the body suit; and the shoulder straps may be attached in an adjustable manner to the body suit when necessary.

3. The device as claimed in claim 2 further comprising a removable brassiere constructed of elastic material and attachment bases which are attached to the brassiere's interior front and rear upper surfaces for attaching the brassiere to the body suit.

4. The device as claimed in claim 3 further comprising a removable brassiere constructed of elastic material with attachable bases which are affixed to the brassiere's exterior surfaces for attachment to the interior of the body suit.

5. The device as claimed in claim 4 further comprising a removable brassiere with adjustable front velcro closure utilizing attachment bases mounted to each front section end.

6. The body suit of claim 1 further comprising a male version of the body suit containing a genitalia pouch comprising:
  (1) two separate crotch bottom ends with each end having attached to it two attachment bases wherein each crotch bottom end may be attached to the other on one of the interior and the exterior of the crotch bottom ends;
  (2) a male genitalia supporting pouch section located within each crotch bottom end between the two attachment bases; wherein the attachment of both crotch bottom ends produces one adjustable male genitalia pouch.

7. The body suit of claim 1 further comprising a male version of the crotch binding further having a genitalia supporting pouch mounted to the center of the crotch binding wherein the elastic waist binding provides therapeutic pressure to the male crotch region while providing concurrent support the male genitalia in tandem with that support provided by the body suit.

* * * * *